United States Patent
Gamiles et al.

(10) Patent No.: US 7,288,770 B2
(45) Date of Patent: Oct. 30, 2007

(54) REAL-TIME UV SPECTROSCOPY FOR THE QUANTIFICATION GASEOUS TOXINS UTILIZING OPEN-PATH OR CLOSED MULTIPASS WHITE CELLS

(75) Inventors: Donald S. Gamiles, Powder Springs, GA (US); Thomas C. Wisniewski, Atlanta, GA (US)

(73) Assignee: Cerex Environmental Services, Clarksville, MD (US)

( * ) Notice: Subject to any disclaimer, the term of this patent is extended or adjusted under 35 U.S.C. 154(b) by 0 days.

(21) Appl. No.: 11/330,368

(22) Filed: Jan. 11, 2006

(65) Prior Publication Data

US 2006/0237657 A1    Oct. 26, 2006

Related U.S. Application Data

(60) Provisional application No. 60/643,329, filed on Jan. 12, 2005.

(51) Int. Cl.
  *G01N 21/64* (2006.01)
(52) U.S. Cl. ............... 250/372; 250/461.1; 356/437
(58) Field of Classification Search ........... 250/372, 250/461.1, 574; 356/437
See application file for complete search history.

(56) References Cited

U.S. PATENT DOCUMENTS

| | | | | |
|---|---|---|---|---|
| 4,050,895 A | * | 9/1977 | Hardy et al. | 436/527 |
| 6,008,928 A | * | 12/1999 | Sachse et al. | 359/246 |
| 6,750,453 B1 | * | 6/2004 | Nelson et al. | 250/338.5 |
| 2002/0085183 A1 | * | 7/2002 | Wu et al. | 355/30 |
| 2004/0155202 A1 | * | 8/2004 | Poteet et al. | 250/461.1 |
| 2005/0219542 A1 | * | 10/2005 | Adams et al. | 356/445 |

OTHER PUBLICATIONS

Dictionary of Economics, Wiley, 1995, s.v. "curve fitting," http://www.xreferplus.com/entry/2764530 (accessed Dec. 11, 2006).*

* cited by examiner

*Primary Examiner*—David Porta
*Assistant Examiner*—Jessica L Eley
(74) *Attorney, Agent, or Firm*—Dennis L. Cook, Esq.

(57) ABSTRACT

The present invention relates, generally, to a portable system for UV spectroscopy capable of the detection and quantification of chemicals from either open air environments or by insertion of a sample using a sample chamber. The system is capable of simultaneously detecting and quantifying chemicals in either a gaseous or liquid form with both sharp and broad spectroscopic features. UV light is generated, collimated into a beam, and focused through a sample volume. The volume can be comprised of an open environment system, or a closed system with a sample cell. The sample cell may contain a number of mirrors which results in one or more "bounces" of light through the volume prior to being focused into a UV Spectrometer. The said light source may be supplied by a variety of sources. Said light is collected and transferred to the processor by short length optical fibers thereby minimizing the light loss in the deep UV.

1 Claim, 4 Drawing Sheets

REAL-TIME UV SPECTROSCOPY FOR THE QUANTIFICATION GASEOUS TOXINS UTILIZING OPEN-PATH OR CLOSED MULTIPASS WHITE CELLS

CROSS-REFERENCE TO RELATED APPLICATION

The present application claims the benefit of previously filed co-pending Provisional Patent Application, Ser. No. 60/643,329 filed Jan. 12, 2005, and incorporates by reference the contents therein.

FIELD OF INVENTION

This invention relates, generally, to a portable system for UV spectroscopy capable of the detection and quantification of chemicals from either open air environments or by insertion of a sample using a sample chamber. The system is capable of simultaneously detecting and quantifying chemicals in either a gaseous or liquid form with both sharp and broad spectroscopic features. UV light is generated, collimated into a beam, and focused through a sample volume. The volume can be comprised of an open environment system, or a closed system with a sample cell. The sample cell may contain a number of mirrors which results in one or more "bounces" of light through the volume prior to being focused into a UV Spectrometer.

BACKGROUND OF THE INVENTION

The use of ultraviolet spectroscopy to detect and quantify compounds in the lab and in the environment is common practice. Many times, the need for the quantification of certain pollutants or toxins are required in real time with reliable results as in the case of chemical spill or industrial accident. Other situations include regular monitoring around power plants or chemical factories or near natural sources of toxic gases such as volcanoes. Conventional open-path UV air monitors require the use of large and complex instruments that have mechanical parts that are expensive to build and maintain. Portable units presently available are limited regarding their detection sensitivity, capability to simultaneously resolve multiple chemicals, the wavelength able to be measured, the ability to quickly de-resolve data, and reliability of calibration.

U.S. Pat. No. 5,485,276 by Bien et al. discloses a multi-pass optical cell for measuring the concentration of one or more species in a fluid to be monitored that includes a sample region; a source of collimated radiation; a detector device for sensing the intensity of the radiation; at least two reflective surfaces for reflecting in a first direction in the sample region a number of times the radiation from the source and delivering it to the detector device. Bien discloses a "multiple" path system, as of the device wherein the sample to be evaluated is bounced back and forth in order to obtain a long enough optical path for accurate measurement. This innovation is meant to overcome a problem in the art regarding pressure drops caused by turbulence that may have deleterious affects on sampling. Bien goes on to disclose the use of a diode laser such as an AlGaAs, InGaAsP, etc. as the collimated radiation. This invention is different from the invention of this application because it uses a detector that is only sensitive to a single wavelength of light.

U.S. Pat. No. 6,750,467 by Tulip discloses a mobile gas detector comprising a laser transmitter and signal analyzer carried on a vehicle, a laser absorption cell carried on the exterior of the vehicle, a light guide connecting light from the laser transmitter into the laser absorption cell, a photo-detector mounted with the laser absorption cell exterior to the vehicle to convert light that has traversed the laser absorption cell into electrical signals, and a cable connecting the photo detector to the signal analyzer. Tulip goes on to describe the apparatus indicating a closed path system and the use of diode laser as the light source. This is different from the invention of this application because a laser is a monochromatic source (single wavelength), whereas this invention uses a broadband source.

Henningsen et al., U.S. Pat. No. 5,946,095, discloses a natural gas detector apparatus as mounted to the vehicle so that the vehicle transports the detector apparatus over an area of interest at speeds of up to 20 miles per hour. This detector invention utilizes a tungsten halogen light source and an optical etalon filter to detect the presence and measure the concentration of either methane or ethane in a path of light. When the light beam passes through the gas, the gas absorbs specific wavelengths of the light, for example, the absorption spectrum at 3.3 microns for methane. By analyzing the absorption of light beam after it has passed through the detection area, the gas may be detected. To detect this absorption, a specific wavelength range of the light may be measured. The wavelength range may be isolated through the use of interference filters and other devices. Also, by measuring the amount of light absorbed, the concentration of the gas may be determined Henningsen is concerned only with natural gas leaks and the quantification of methane or ethane as determined via the absorption of these two gases by the light source as analyzed spectrally. This is different from the invention of this application because it utilizes single frequency infrared energy.

U.S. Pat. No. 6,750,453 by Nelson et al., discloses a system to measure two gas targets such as ethane and methane separately yet simultaneously using a gas correlation radiometer. Nelson discloses a source that directs broadband modulated light into a region of free atmosphere in which target gas may be present. A gas correlation radiometer responds to light transmitted through the region. Separate radiometer channels respond to a single beam of light after transmission through the region. A beam splitter separates the beam into two beams, one directed into each of the channels. The two channels separately and simultaneously respond to a respective one of the light beams for separately and simultaneously generating signals that together indicate whether the target gas is in the free atmosphere. The method provides an optimal bandpass of an IR filter that filters the light before transmission to the radiometers. Another method uses a null factor in computing an output that determines the concentration of the target gas in the free atmosphere. The invention of this application uses a UV source not an IR source None of these prior art systems or devices describe a system comprising an open-path UV monitoring system that simultaneously detects and quantifies gases with both sharp and broad spectral features and a conventional open-path UV monitor capable of using a variety of broad-band UV sources or blackbody sources with great flexibility and accuracy.

Therefore, there is a need for a open-path UV spectroscopic air monitoring system capable of operating using a variety of broadband UV sources or black body sources, is able to collect high resolution data for subsequent de-resolution for analysis of species such as 1-3 Butadiene, Hydrogen Sulfide, and Acrolein, that possesses a background update routine for updating clean air backgrounds, and that utilizes small length optical fibers between the source collection point and the diode array detectors thereby minimizing the light loss in the deep UV (less than 210 nm).

It is another object of this invention to provide a portable open path UV spectroscopic air monitoring system that is able to utilize a variety of broadband UV sources such as Xenon and Deuterium lamps.

It is another object of this invention to provide an apparatus that sends a beam of light into the open air to a receiver that focuses the beam into a UV Spectrometer and thereby using spectroscopy to analyze the gases that cross the beam path for specific chemicals and their respective concentrations.

It is the object therefore of this invention to provide a portable apparatus for measuring a property of a sample using a multipass, or white cell, UV source, set of mirrors to facilitate a multi pass system, detection array, and a processor.

It is another object of this invention to provide a portable apparatus with a closed path apparatus wherein the internal environment is purged of oxygen facilitating the measure in the 160-210 nanometer wavelength range for gaseous compounds that have characteristic spectral absorbance features within this spectral region.

It is yet another object of this invention to provide a portable open path or closed cell apparatus with a system that can collect high resolution data and that can be then de-resolved to analyze for species such as 1-3 Butadiene, Hydrogen Sulfide, and Acrolein.

It is yet another object of this invention to provide a portable open path or closed cell apparatus with data analysis software algorithm routine utilizing a background update routine that automatically, and iteratively updates the clean air background for a specific chemical if it is not detected during the last collection cycle.

By purging the closed path system of oxygen, the apparatus can measure in the 160-200 nm wavelength range. This enables the detection of gases such as butadiene, hydrogen sulfide, butane, and propane. Due to the enhanced sensitivity provided by the increased beam path caused by multiple mirrors (2), the system collects high resolution data that can then be de-resolved to analyze for species such as 1-3 Butadiene, Hydrogen Sulfide, and Acrolein.

It is yet another object of this invention to utilize multiple regression analysis when performing simultaneous real-time multiple compound detections to quantify results and to use Partial Least Squares (PLS) regression to identify and quantify certain unknown gases contained within a sample.

This and other objects of the invention will in part be obvious and will in part appear hereinafter.

BRIEF DESCRIPTION OF THE FIGURES

The invention will now be described, by way of example only, with reference to the accompanying figures in which.

ITEMS OF THE FIGURES

Figure 1:
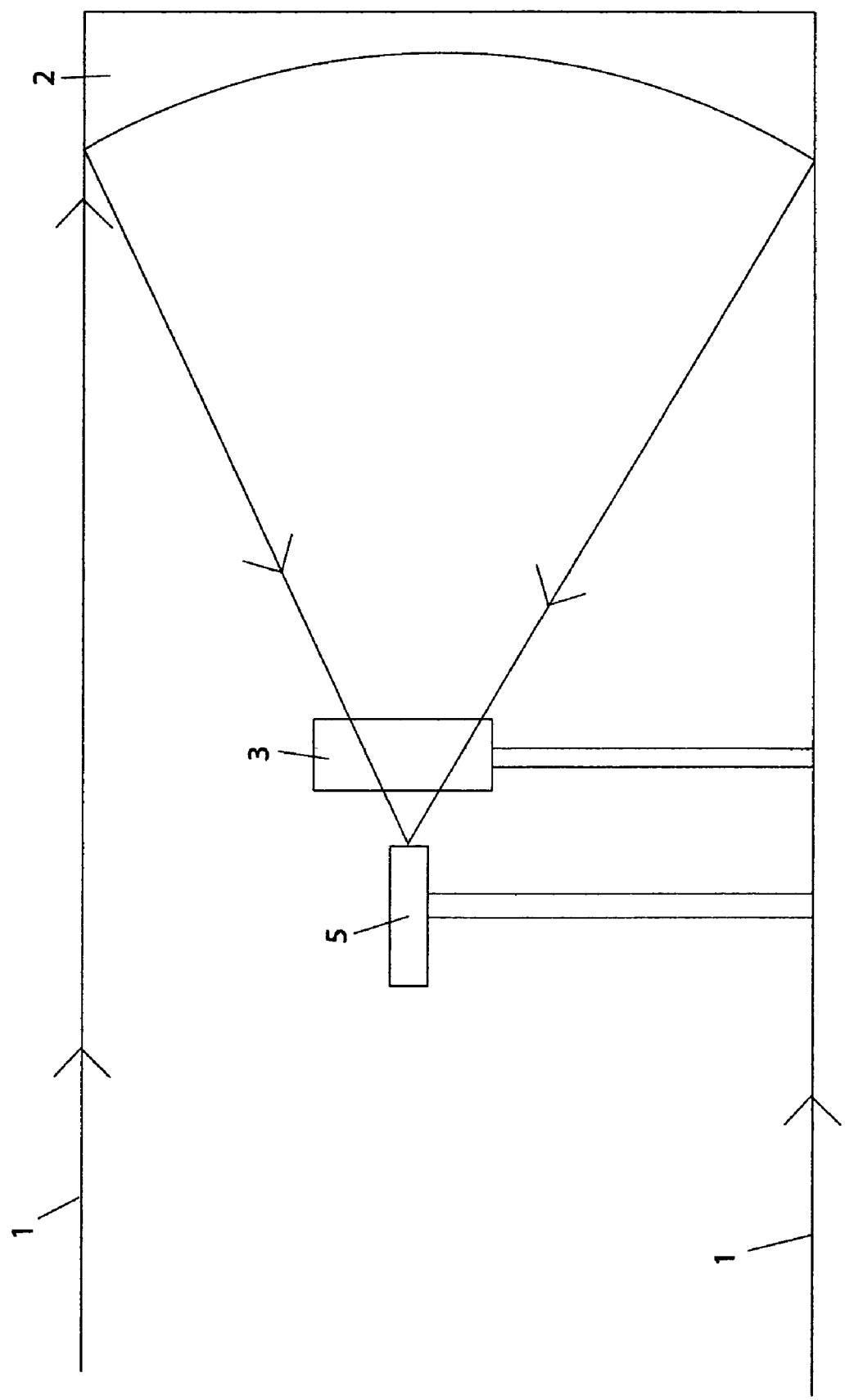
FIG. 1 is an open path receiver drawing illustrating the path of the UV light.

1. Light from light source
2. Focusing mirror
3. Sample holder for the calibration cell
4. Detector Array
5. Fiber optic coupling
6. Lens
7. Input fan
8. Exit port
9. Optical fibers
10. Light source
11. Portable Apparatus

SUMMARY OF THE INVENTION

This invention relates to a portable air monitoring system that is based on UV spectroscopy that can operate either in an open or closed path system. The apparatus relates to the detection and quantification of chemicals either in the open air environment or a sample that is inserted into a chamber. The apparatus is capable of simultaneously detecting and quantifying gases with both sharp and broad features. The apparatus functions on the principle of collecting a full spectrum (large bandwidth) of data points and therefore affords the capability to perform real-time multi-gas analysis. Gases that are able to be detected include but are not limited to: Bromine, Chlorine, Chlorine Dioxide, Carbon Monoxide, Carbon Dioxide, Phosgene, Hydrogen Bromide, Hydrogen Chloride, Mustard Gas, Nitrous acid, Nitrous oxide, Nitrate radical, Oxygen, Sulfur trioxide, hydrocarbons, Naftalene, Acethylene, Ethene, Ethane, Ethanol, Propane, Trimethylbenzene, o-, m-, p-Xylene, Sarin, Styrene, Phenol, o-,m-,p-Cresol, Butane, Acrolein, 1-3 Butadiene, Benzene, and Methanol.

One version of the apparatus measures a property of a sample using a white cell. The apparatus includes a UV source and a set of mirrors that bounce the beam back and forth until it is focused down to a collection element, a detection array, and a processor. By bouncing the beam between the mirrors, the sample path is extended and the lower detection capability of the system is substantially enhanced. This apparatus is then able to be mounted on a vehicle (such as airplane or motor vehicle) and used to determine the presence of various gases simultaneously in the sample.

A second version of the apparatus uses a beam of light that is directed into an open air receiver. Telescope optics then focus the beam onto a collection element, and then finally into a UV Spectrometer. Using absorption spectroscopy, the gases that cross the beam path can be analyzed for both specific chemical species and their respective concentration.

Further, another version uses a small sample cell of between 0.001 to 1 meter in length to measure the concentration of either high concentrations of gas or liquid samples. This version has applications in industrial stack and process monitoring.

The apparatus has the capability of being operated using a variety of broadband UV sources such as Xenon and Deuterium lamps. Enhanced measurement is provided by purging the closed path systems of all oxygen, the apparatus can measure gases in the 160-210 nm wavelength range enabling the detection of gases with deep-UV absorption features. Gas candidates in this family include, but are not limited to hydrogen sulfide, butane, and propane. The system collects high resolution data, but can be de-resolved to analyze for broad-featured species such as 1-3 Butadiene, Hydrogen Sulfide, and Acrolein.

Continuous real-time monitoring of the apparatus is enhanced by a data analysis software algorithm routine utilizing a background update routine that automatically, and iteratively updates the clean air background for a specific chemical if it is not detected during the last collection cycle.

The use of small (less than 1 meter) length optical fibers between the source collection point and the diode array detectors minimizes the amount of light loss in the deep UV (less than <210 nm) which is critical for the detection of 1-3 Butadiene, Hydrogen Sulfide, Butane, and Acrolein.

The apparatus and system of this invention utilizes multiple regression analysis when performing simultaneous real-time multiple compound detections in order to quantify results. When certain unknown gases are present within a sample, Partial Least Squares (PLS) regression is used to identify and quantify said gases.

The combination of short length optical fibers, small UV broadband sources, and diode array detectors allows the apparatus to be small, portable, field reliable, and sensitive to small amounts of constituents or chemical species of interest. Furthermore, this configuration can provide an inexpensive apparatus that could permit the continuous testing of the chemical components in air or other fluid medium.

DESCRIPTION OF THE PREFERRED EMBODIMENT

Figure 2:
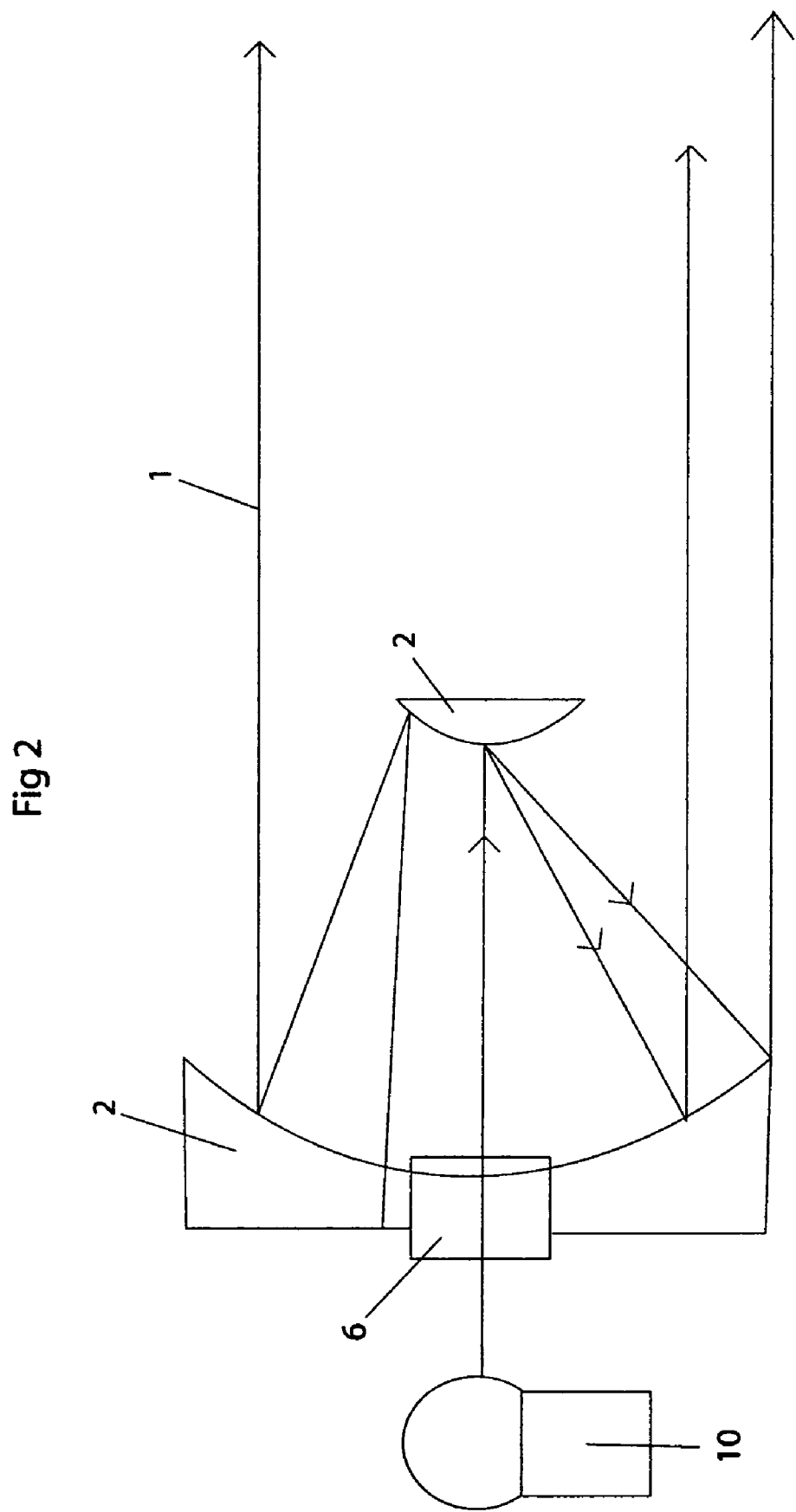
FIG. 2 shows a cross section view of the open path source of the apparatus.

The present invention in an open path embodiment is disclosed in FIGS. 1 and 2. FIG. 2 shows the transmitter of the open path apparatus wherein the light (1) from the light source (10) is sent through a focusing lens (6), then to a set of mirrors (2). The mirrors (2) in this embodiment direct the focused light to the receiver In receiver of the open path apparatus shown in FIG. 1, the light is collected by a mirror (2), through a calibration cell (3) if desired, and then to a fiber optic coupling (5) that leads to a detector (not shown in FIG. 1) for analyzing. The apparatus has the capability and flexibility of being operated using a variety of broadband UV sources such as Xenon or Deuterium lamps. The open-path air monitor of this invention also has the capability of being operated in a passive mode using either direct sunlight or a blackbody source such as volcano, oil refinery flare, tanker fire, and so on.

Figure 3:
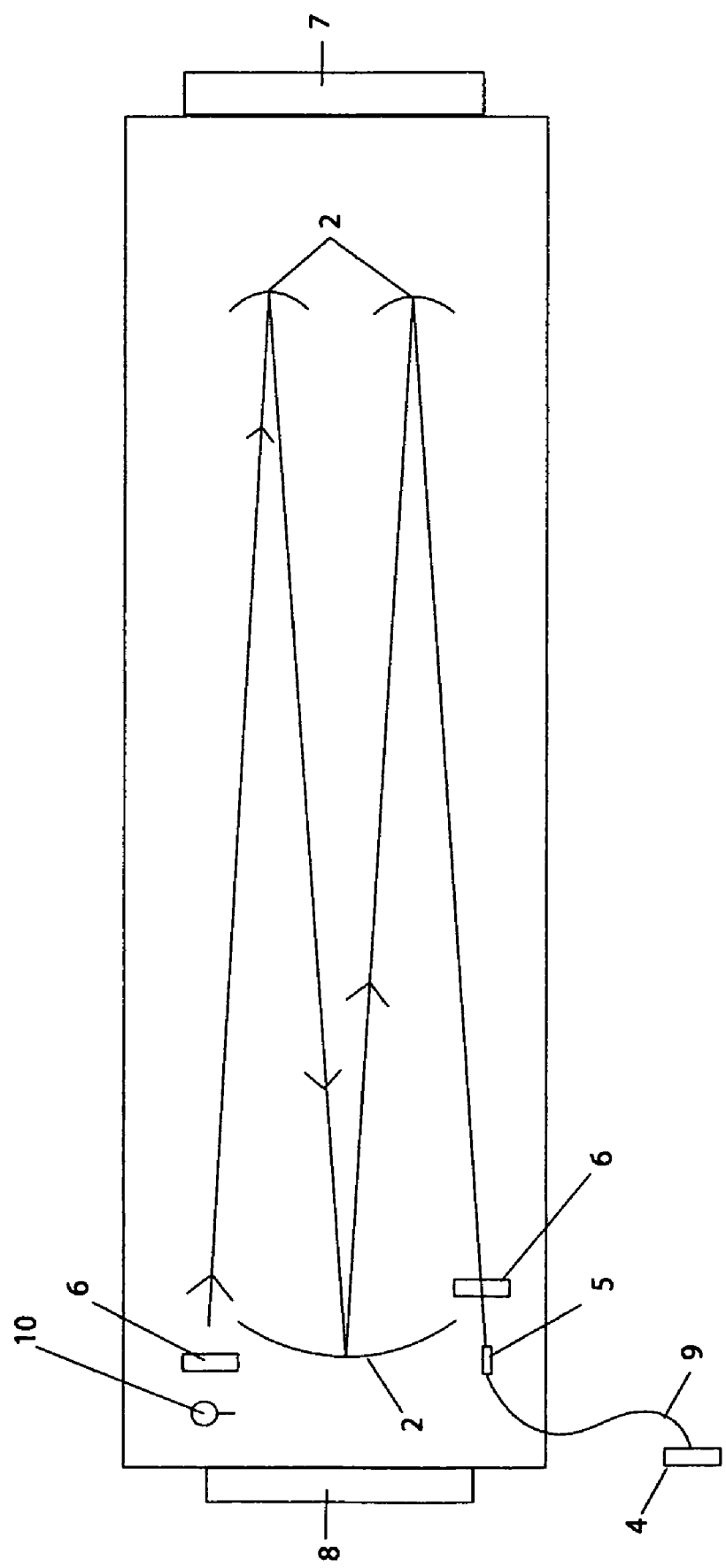
FIG. 3 shows a cross section drawing of a closed path portable apparatus with a multipass cell; and, FIG. 4 is an environment view of the portable apparatus as fixed to an automobile.

FIG. 3 is a schematic for a portable apparatus (11) showing a light source (10) that is generated and directed through the lens (6) to a series of mirrors (2) in order to extend the path length of the light thereby enhancing the detection capability. The apparatus may be operated using a one, two, or multipass white cell optical configuration to develop the appropriate path length required to achieve the desired end detection level for the gas(es) of interest. The sample to be analyzed is drawn into the chamber of the apparatus via the input fan (7), travels through the apparatus wherein specific absorption of the light beam occurs, and exits via the exit port (8). The light beam travels through the chamber a number of times, and thus the sample, through another lens (6), is collected by the fiber optic coupling (5), travels then via optical fibers (9) to the detection array (4), and subsequently to a processor (not shown) in order to be analyzed. Using absorption spectroscopy, the gases that cross the beam path can be analyzed for both the specific chemicals being detected and their respective concentrations. Analysis of said chemicals is via spectroscopic techniques. The use of short length optical fibers (9) of less than 1 meter long, minimizes the light loss in the deep UV (<210 nm) and further enhances the accuracy and sensitivity of measurement.

By purging the closed path system of oxygen, the apparatus can measure in the 160-200 nm wavelength range. This enables the detection of gases such as butadiene, hydrogen sulfide, butane, and propane. Due to the enhanced sensitivity provided by the increased beam path caused by multiple mirrors (2), the system collects high resolution data that can then be de-resolved to analyze for species such as 1-3 Butadiene, Hydrogen Sulfide, and Acrolein. The system can also be used to quantify chemical weapons material.

Figure 4:
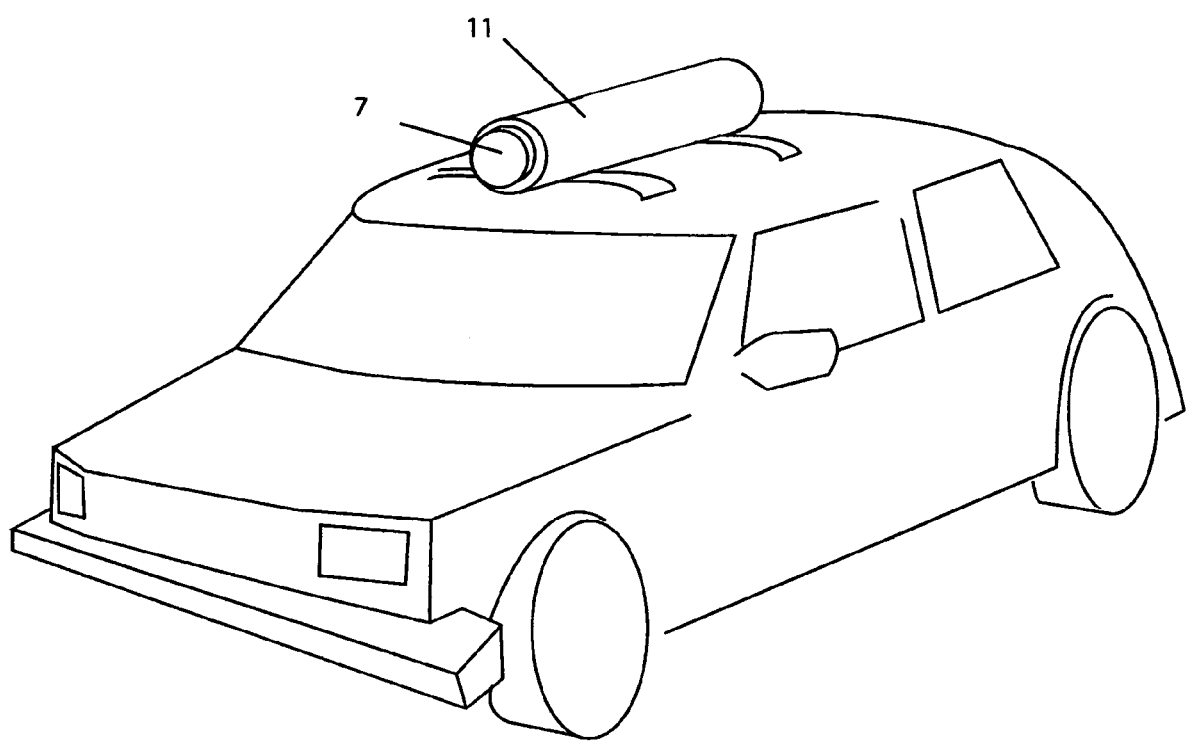

FIG. 4 shows an environmental view wherein the entire portable apparatus (11) is mounted atop of a vehicle for the detection and quantification of specific chemicals. Alternatively, the apparatus may be mounted strategically near locations wherein the detection of specific airborne chemicals is of importance such as chemical manufacturing plants, power plants, and mining operations.

The apparatus utilizes a spectrometer for the analysis of the gas samples that easily identifies spectral features of gases commonly seen at, but not limited to, petroleum refineries, industrial sites, ambient air monitoring stations, and livestock operations. The use of a miniature spectrometer with no moving parts and low weight affords high reliability to the portable apparatus. As the apparatus may be made from light weight materials coupled with the small size of the spectrometer, the entirety of the apparatus is extremely lightweight, approximately 30 pounds.

Multiple regression analysis is utilized when performing simultaneous real-time multiple component compound detections in order to quantify results. When unknown gases are contained within a sample, a Partial Least Squares (PLS) regression is used to identify and quantify the chemicals.

The apparatus connects directly to a lap top computer via a standard USB port and standard Microsoft Windows based software is used to acquire, record, and report data. Data acquisition is near instantaneous with single scan data acquisition of approximately 0.2 seconds per scan.

Although this invention has been described in the form of a preferred embodiment, many modifications, additions, and deletions, may be made thereto without departure from the spirit and scope of the invention, as set forth in the following claims.

What is claimed is:

1. A portable chemical detection apparatus for measuring the chemical properties of a sample gas or fluid within a sample chamber comprising:

an Ultra Violet light source;

transmitter optics situated by said Ultra Violet light source such that said transmitter optics transmit a collimated beam of Ultra Violet light into a sample chamber;

receiver optics situated such that once the collimated beam of Ultra Violet light has passed through the sample chamber said receiver optics receives said collimated beam of Ultra Violet light and focuses said collimated beam of Ultra Violet light onto a fiber optic coupling device;

said fiber optic coupling device optically connected to a optical fiber such that said fiber optic coupling device transmits the collimated beam of Ultra Violet light into said optical fiber;

a detection array optically connected to said optical fiber; and a processor in communication with said detection array and capable of processing the detected information from said detection array and determining chemical compositions from the detected information wherein the detection apparatus is a closed path apparatus wherein the internal environment of the detection apparatus is capable of being purged of oxygen thereby facilitating measurement in the 160-210 nanometer wavelength range for gaseous compounds that have characteristic spectral absorbance features within this spectral region.

* * * * *